United States Patent
Ihn

(10) Patent No.: US 7,822,573 B2
(45) Date of Patent: *Oct. 26, 2010

(54) METHOD AND APPARATUS FOR MODELING RESPONSES FOR A MATERIAL TO VARIOUS INPUTS

(75) Inventor: Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 327 days.

This patent is subject to a terminal disclaimer.

(21) Appl. No.: 11/840,427

(22) Filed: Aug. 17, 2007

(65) Prior Publication Data

US 2009/0048721 A1    Feb. 19, 2009

(51) Int. Cl.
G06F 17/00    (2006.01)
(52) U.S. Cl. ............... 702/113; 702/34; 702/35; 702/36; 73/579; 73/583
(58) Field of Classification Search ............. 702/34–36, 702/113; 73/579, 583
See application file for complete search history.

(56) References Cited

U.S. PATENT DOCUMENTS 6,006,163 A * 12/1999 Lichtenwalner et al. ....... 702/36
2009/0083004 A1 * 3/2009 Ihn et al. .................... 702/189

OTHER PUBLICATIONS

Wang et al., "A synthetic time-reversal imaging method for structural health monitoring", Institute of Physics Publishing, Smarter Materials and Structures 13 (2004), U.K., pp. 415-423.
Leutenegger et al., "Detection of defects in cylindrical structures using a time reverse method and a finite-difference approach", May 2002, pp. 721-725, vol. 40, Issues 1-8, Ultrasonics.
Leutenegger et al., "Non-destructive testing of tubes using a time reverse numerical simulation (TRNS) method", May 2004, pp. 811-822, vol. 41, Issue 10, Ultrasonics.
GB Search Report for application No. GB0812572.6 dated Nov. 2008.
Shi et al., "Identification of Time-Domain Reflectometry Measurements Results", Proceedings of International Workshop on Structural Health Monitoring, 2001, pp. 1269-1278.

* cited by examiner

*Primary Examiner*—Sujoy K Kundu
(74) *Attorney, Agent, or Firm*—Yee & Associates, P.C.; John A. Lepore

(57) ABSTRACT

A computer implemented method, apparatus, and computer usable program code for testing a material. A signal is sent into the material using the transmitter. The signal has a frequency range that falls within a selected frequency range to form a transmitted signal. An actual response to the transmitted signal is received at a sensor. A simulated response of the material to the transmitted signal is generated using a functional model capable of modeling responses of the material to different frequency ranges falling within the selected frequency range. The simulated response is compared to the actual response to determine if a change has occurred in the material.

6 Claims, 6 Drawing Sheets

METHOD AND APPARATUS FOR MODELING RESPONSES FOR A MATERIAL TO VARIOUS INPUTS

BACKGROUND INFORMATION

1. Field

The present disclosure relates generally to processing data, in particular, to generating simulated responses of a material to input. Still more particularly, the present disclosure relates to a method, apparatus, and computer usable program code for simulating responses of a material to input using a model.

2. Background

Structural health monitoring techniques have been developed and used to monitor materials and structures. These techniques often build the health monitoring systems into structures. These health monitoring systems may be used to determine whether changes have occurred to these materials and structures over time. Sudden changes in environments, such as electromagnetic effects, mechanical stresses, and other environmental effects may affect the integrity of various materials and structures over time. By having health monitoring systems built in to or associated with the structures to monitor the structures during use, appropriate measures and responses may be taken to prevent catastrophic failures and may prolong the life span of these structures.

Monitoring of structures may include various non-destructive elevation methods, such as ultrasonic testing or x-ray testing. Ultrasonic testing uses contact-based transducers to mechanically scan a structure. These distributed sensors and actuators may be surface mounted on the structure or even embedded in the structure to generate and propagate control of diagnostic signals into the structure being monitored.

A structural health monitoring system is based on using a transmitter and a sensor configuration to transmit waveforms at various frequency ranges and acquire data from the responses. Oftentimes, transducers may function both as a transmitter and a sensor.

An optimal waveform cannot be determined ahead of time because of the lack of information. As a result, a large number of input waveforms having different frequency ranges are used. Large amounts of data are recorded from the responses to prevent missing any information that may be needed. The need to use input waveforms or signals at different frequencies occurs because many parameters are present for optimization. For examples, these parameters include driving frequency, time duration, number of cycles, window function for amplitude modulation, and other factors.

Further, in a structural health monitoring system, different processes may be executing that focus on different structural and damaged properties. These different processes may require multiple sets of input signals to obtain the responses or data needed by the different processes.

When a structure is first manufactured or produced, a baseline or initial set of data is collected for use in future comparisons. This baseline or initial set of data is a set of responses collected for different frequency ranges for use in future comparisons. This initial set of data assumes that the structure is in a desired condition without any defects that may cause failures.

All of the response data collected by the different input signals are saved in the database. By having to initially input signals at various frequency ranges, in addition to replicating frequency ranges for other parameters, the amount of data collected is large and takes up a considerable amount of space in a structural health monitoring system.

Therefore, it would be desirable to reduce the amount of data that has to be saved for a structural health monitoring system.

SUMMARY

The different advantageous embodiments provide a computer implemented method, apparatus, and computer usable program code for testing a material. A signal is sent into the material using the transmitter. The signal has a frequency range that falls within a selected frequency range to form a transmitted signal. An actual response to the transmitted signal is received at a sensor. A simulated response of the material to the transmitted signal is generated using a functional model capable of modeling responses of the material to different frequency ranges falling within the selected frequency range. The simulated response is compared to the actual response to determine if a change has occurred in the material.

In another advantageous embodiment, structures are monitored in a vehicle. A signal having a frequency range is sent into a structure in the vehicle from a fixed transmitter associated with the structure. A response to the signal is received at a fixed sensor associated with the structure. Parameters are input into a transfer function to simulate sending the signal having the frequency range into the structure by the fixed transmitter. A simulated response is received that simulates the response received by the fixed sensor in response to inputting the parameters. A determination is made as to whether the response matches the simulated response. A warning indicator is generated if a match between the response and the simulated response is absent.

In yet another embodiment, the apparatus has a structure, a set of transmitters, a set of sensors, and a structural health monitoring system. The structure has a plurality of components. The set of transmitters are capable of sending signals into the plurality of components. The set of sensors are capable of detecting responses to the signals. The structural health monitoring system receives an actual response to the transmitted signal from a sensor in the set of sensors, generates a simulated response of the component to the transmitted signal using a functional model capable of modeling responses of the component to different frequency ranges falling within the selected frequency range, and compares the simulated response to the actual response to determine if a change has occurred in the material.

Still, another embodiment comprises a computer program product on a computer usable medium having computer usable program code for monitoring structures in a vehicle. Computer usable program code is present to send a signal having a frequency range into a structure in the vehicle from a fixed transmitter associated with the structure. The computer program product includes computer usable program code to receive a response to the signal at a fixed sensor associated with the structure. Computer usable program code is present to input parameters into a transfer function to simulate sending the signal having the frequency range into the structure by the fixed transmitter. Computer usable program code is present to receive a simulated response that simulates the response received by the fixed sensor in response to inputting the parameters. The computer program product includes computer usable program code to determine whether the response matches the simulated response. Computer usable program code is present to generate a warning indictor if a match between the response and the simulated response is absent.

In yet another embodiment, a computer program product comprises a computer usable medium having computer usable program code for testing a material. Computer usable program code is present to send a signal into the material using the transmitter, wherein the signal has a frequency range that falls within a selected frequency range to form a transmitted signal. The computer program product includes computer usable program code to receive an actual response to the transmitted signal at a sensor. The computer program product also includes computer usable program code to generate a simulated response of the material to the transmitted signal using a functional model capable of modeling responses of the material to different frequency ranges falling within the selected frequency range. Computer usable program code is present to compare the simulated response to the actual response to determine if a change has occurred in the material.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
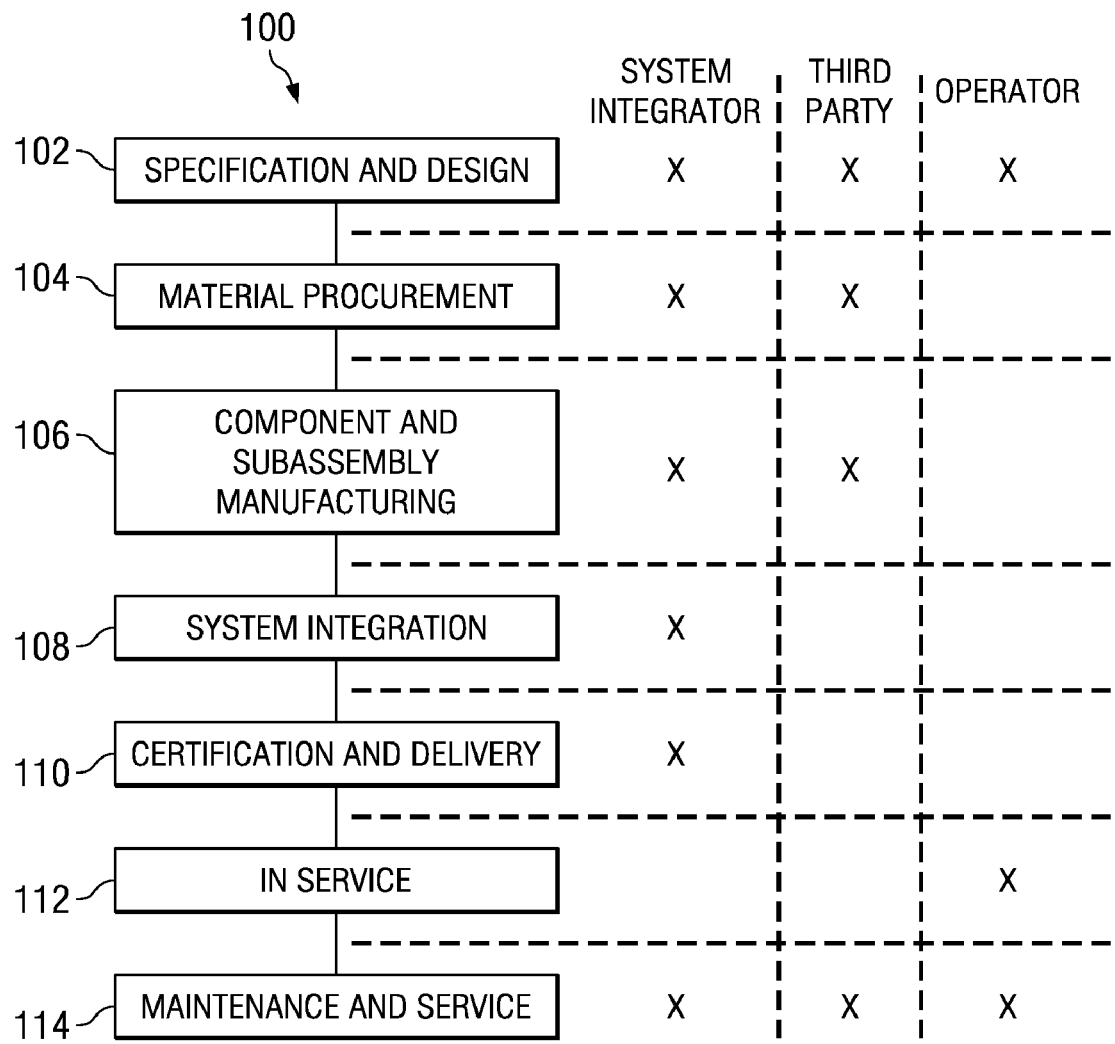
FIG. 1 is a diagram illustrating an aircraft manufacturing and service method in accordance with an advantageous embodiment.
Figure 2:
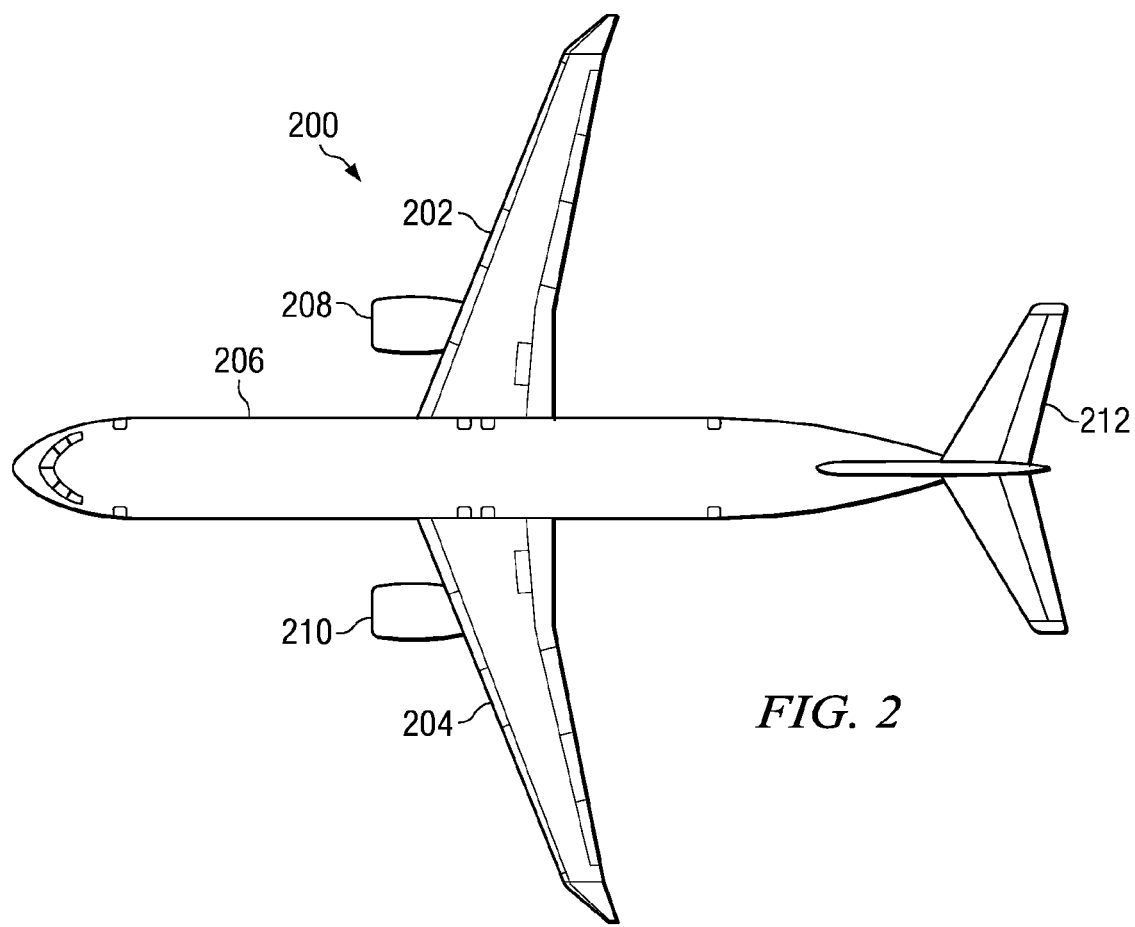
FIG. 2 is a diagram of an aircraft in accordance with an advantageous embodiment.

Referring more particularly to the drawings, embodiments of the disclosure may be described in the context of the aircraft manufacturing and service method as shown in FIG. 1 and the aircraft as shown in FIG. 2. Turning first to FIG. 1, a diagram illustrating an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of method 100 may be performed or carried out by a system integrator, a third party, and/or an operator as indicated by the "X" in the grid to the right of the flow diagram of FIG. 1. In these examples, the operator may be a customer. For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 has wings 202 and 204 attached to body 206. Aircraft 200 includes wing mounted engine 208, wing mounted engine 210, and tail 212. Aircraft 200 is produced by aircraft manufacturing and service method 100.

Apparatus and methods embodied herein may be employed during any one or more of the stages of production and service method 100 in FIG. 1. For example, components or subassemblies corresponding to component and subassembly manufacturing 106 may be fabricated or manufactured in a manner similar to components or subassemblies produced while aircraft 200 is in service. Also, one or more apparatus embodiments, method embodiments, or a combination thereof may be utilized during production stages for component and subassembly manufacturing 106 and system integration 108 in FIG. 1, for example, by substantially expediting assembly of or reducing the cost of aircraft 200. Similarly, one or more of apparatus embodiments, method embodiments, or a combination thereof may be utilized one of during different stages, such as component and subassembly manufacturing 106, and system integration 108, in service 112, and/or routine maintenance and service 114 of aircraft 200 in FIG. 2.

Figure 3:
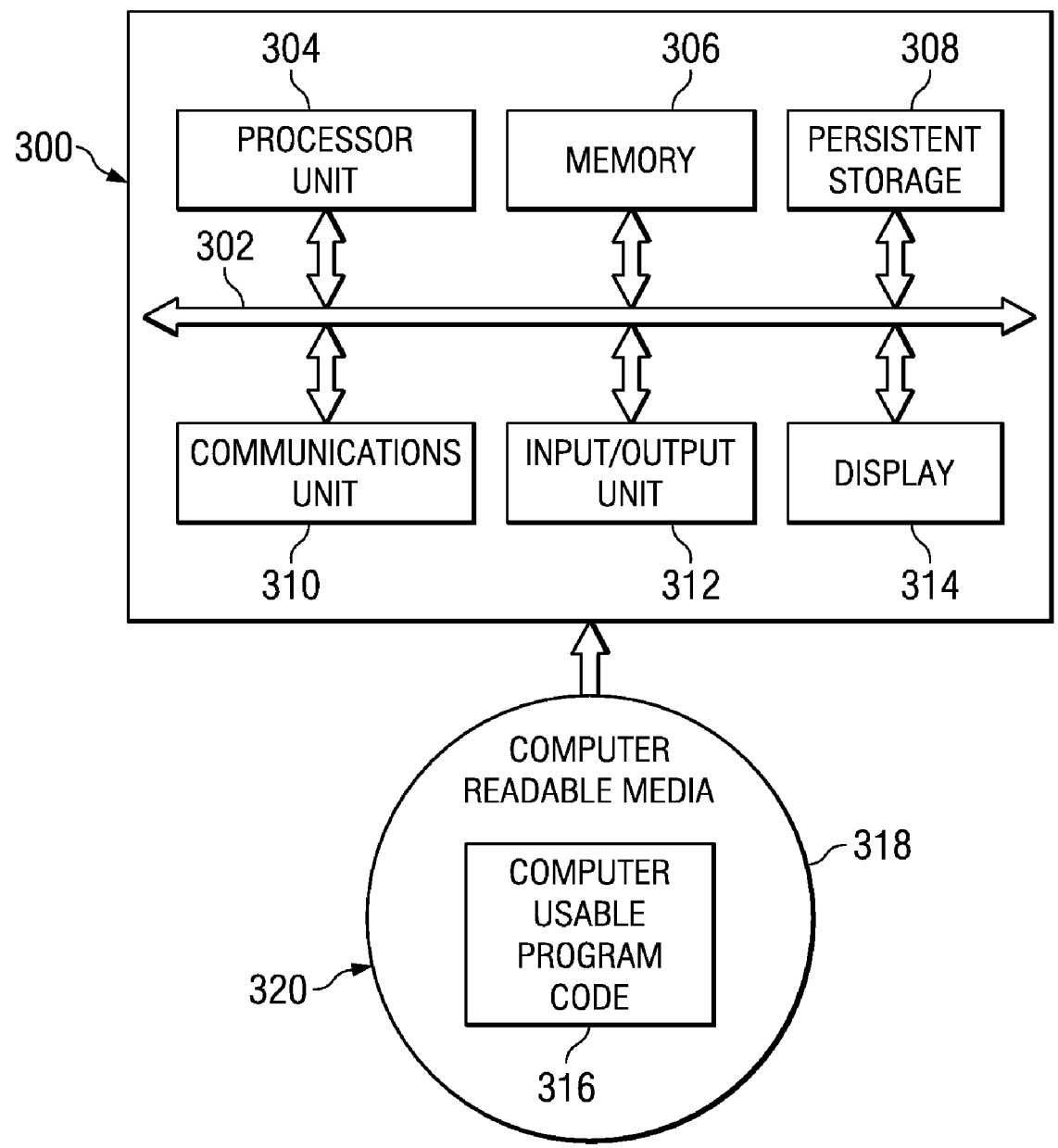
FIG. 3 is a diagram of a data processing system in accordance with an advantageous embodiment.

Turning now to FIG. 3, a diagram of a data processing system is depicted in accordance with an advantageous embodiment. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multiprocessor core, depending on the particular implementation. Further, processor unit 304 may be implemented using one or more heterogeneous processor systems in which a main processor is present with secondary processors on a single chip. As another illustrative example, processor unit 304 may be a symmetric multiprocessor system containing multiple processors of the same type.

Memory 306, in these examples, may be, for example, a random access memory. Persistent storage 308 may take various forms depending on the particular implementation. For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard and mouse. Further, input/output unit 312 may send output to a printer. Display 314 provides a mechanism to display information to a user.

Instructions for the operating system and applications or programs are located on persistent storage 308. These instructions may be loaded into memory 306 for execution by processor unit 304. The processes of the different embodiments may be performed by processor unit 304 using computer implemented instructions, which may be located in a memory, such as memory 306. These instructions are referred to as computer usable program code or computer readable program code that may be read and executed by a processor in processor unit 304.

The computer readable program code may be embodied on different physical or tangible computer readable media, such as memory 306 or persistent storage 308.

Computer usable program code 316 is located in a functional form on computer readable media 318 and may be loaded onto or transferred to data processing system 300. Computer usable program code 316 and computer readable media 318 form computer program product 320 in these examples. In one example, computer readable media 318 may be, for example, an optical or magnetic disc that is inserted or placed into a drive or other device that is part of persistent storage 308 for transfer onto a storage device, such as a hard drive that is part of persistent storage 308. Computer readable media 318 also may take the form of a persistent storage, such as a hard drive or a flash memory that is connected to data processing system 300.

Alternatively, computer usable program code 316 may be transferred to data processing system 300 from computer readable media 318 through a communications link to communications unit 310 and/or through a connection to input/output unit 312. The communications link and/or the connection may be physical or wireless in the illustrative examples. The computer readable media also may take the form of non-tangible media, such as communications links or wireless transmissions containing the computer readable program code.

The different components illustrated for data processing system 300 are not meant to provide architectural limitations to the manner in which different embodiments may be implemented. The different illustrative embodiments may be implemented in a data processing system including components in addition to or in place of those illustrated for data processing system 300. Other components shown in FIG. 3 can be varied from the illustrative examples shown.

The different advantageous embodiments recognize that the current techniques used to create models for structural health monitoring systems take up large amounts of space. In some applications, when a structure takes the form of a building or a dam, the amount of space used to save data in a structural health monitoring system may not be of concern. In other applications, however, such as in an aircraft or a spacecraft, minimizing data storage is essential because of limited storage space in these types of structures.

Thus, the different advantageous embodiments provide a capability to regenerate, or simulate, different input responses with varying parameters through virtual simulations, rather than using data from actual tests to identify responses for comparison. In other words, rather than using a model that contains data that is identified in response to different inputs to generate the responses for comparison to actual monitoring responses, the different advantageous embodiments provide a functional model which generates simulated responses in response to the input.

The different advantageous embodiments provide a method, apparatus, and computer usable program code for testing a material for a structure. In one embodiment, a signal is sent into a material using a transmitter in which the signal has a frequency range that falls within a selected frequency range. An actual response to the transmitted signal is received at the sensor. A simulated response of the material to the first frequency range is made using a functional model capable of modeling responses of the material to different frequency ranges falling within the selected frequency range. The simulated response is compared to the actual response to determine if a change has occurred in the material.

In another embodiment, structures in a vehicle may be monitored. A signal having a frequency range is sent into a structure in the vehicle from a fixed transmitter associated with the structure. A response to the signal is received at the fixed sensor associated with the structure. Thereafter, parameters are input into a transfer function to simulate sending the signal having the frequency range into the structure by the fixed transmitter. In response to inputting these parameters, a simulated response is received that simulates the response received by the fixed sensor. A determination is made as to whether the response matches the simulated response. A warning is generated if a match between the response and the simulated response is absent. In these different embodiments, a match may be an exact match between the actual response and the simulated response. A match also may be present if the differences between the actual response and the simulated response fall within some range or margin of error.

Figure 4:
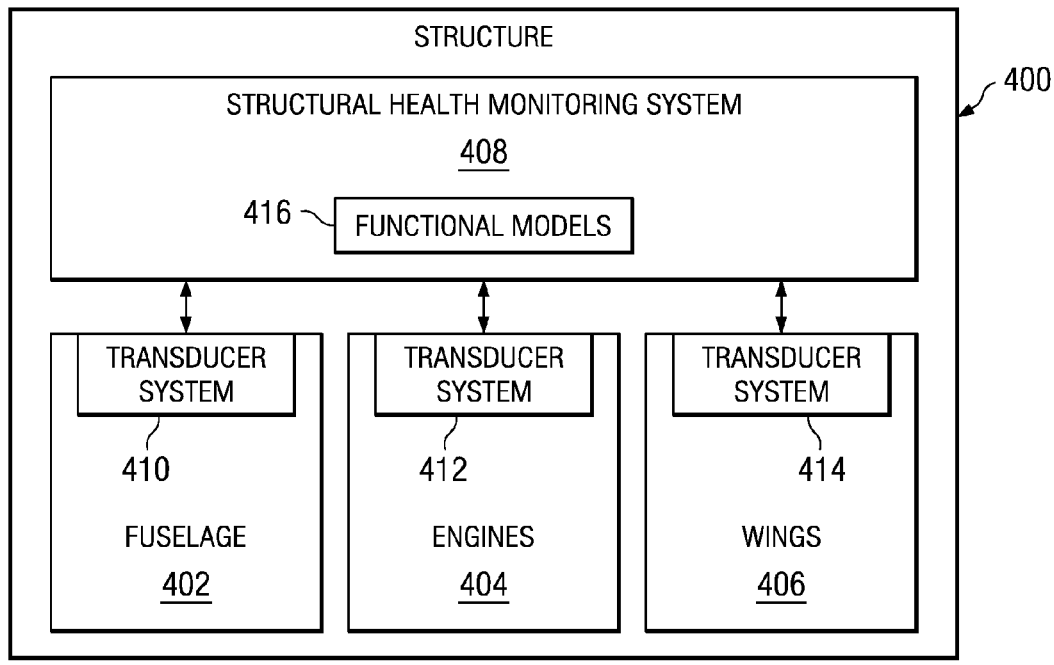
FIG. 4 is a diagram illustrating components used for structural health monitoring in a structure in accordance with an advantageous embodiment.

Turning now to FIG. 4, a diagram illustrating components used for structural health monitoring in a structure is depicted in accordance with an advantageous embodiment. Structure 400 is an example of a structure in which a health monitoring system may be implemented. Structure 400 may take many forms, such as an aircraft, a car, a tank, a ship, a submarine, a spacecraft, a dam, a building, or a bridge.

In this example, structure 400 takes the form of an aircraft. Structure 400 includes fuselage 402, engines 404, and wings 406. Other components also are found in structure 400, but only these depicted ones are presented for purposes of illustrating different features in the different advantageous embodiments.

Structure 400 also includes structural health monitoring system 408, transducer system 410, transducer system 412, and transducer system 414. Although transducers are used for transmitters and sensors in these examples, any type of transmitter, sensor, or device may be used that is capable of sending and detecting signals at the frequencies needed to transmit the signals into a material.

Structural health monitoring system 408 may be implemented in structure 400 using a data processing system, such as data processing system 300 in FIG. 3. Structural health monitoring system 408 may take the form of software, hardware, or a combination of software and hardware. In this example, structural health monitoring system 408 is implemented in software using a data processing system, such as data processing system 300 in FIG. 3.

Transducer systems 410, 412, and 414 are examples of transmitters and sensors that may be implemented in structure 400 to transmit signals and detect responses to those signals. In these examples, the transducers in these systems are "associated" with the particular components in structure 400. A transmitter or sensor, such as those in transducer systems 410, 412, and 414, may be physically associated with the component by being attached to the component or even embedded within the component. In these examples, the transducers are fixed transmitters and fixed sensors that are not moved once they are placed.

In this depicted example, transducer system 410 is a set of one or more transducers that is placed onto or within fuselage 402. Transducer system 410 may be attached to surfaces within fuselage 402 or may be embedded into the materials itself, depending on the particular implementation. The different transducers within transducer system 410 are arranged to be capable of monitoring one or more areas within fuselage 402. These areas may be selected based on different factors, such as identifying areas in which damage may cause a failure within fuselage 402. In a similar fashion, transducer system 412 is attached to or integrated with components in engines 404. Transducer system 414 also is integrated and configured to collect data from one or more areas in wings 406.

Transducer systems 410, 412, and 414 are controlled by structural health monitoring system 408. Structural health monitoring system 408 may send signals for transmission by these transducer systems. Further, the responses received to these signals are returned to structural health monitoring system 408 for processing. The responses collected from transducer systems 410, 412, and 414 are compared to simulated responses generated by functional models 416.

Functional models 416 contain models that simulate responses for different transducers and receivers for different frequency ranges, in these examples. A functional model may be present for each transmitter and receiver configuration to simulate the response that is detected by a particular sensor when a particular transmitter is used. Thus, a different functional model may be present for the same sensor when a signal is transmitted by different transmitters, in these examples.

Figure 5:
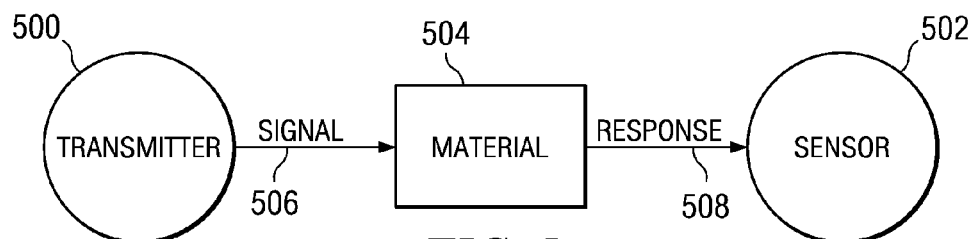
FIG. 5 is a diagram illustrating signal transmission and detection in accordance with an advantageous embodiment.

Turning now to FIG. 5, a diagram illustrating signal transmission and detection is depicted in accordance with an advantageous embodiment. In this example, transmitter 500 and sensor 502 are used to test material 504. Transmitter 500 and sensor 502 are an example of a transmitter and sensor that may be found in transducer system 410 in FIG. 4. Material 504 is an example of a material that is present in a structure, such as fuselage 402 or wings 406 in FIG. 4.

Transmitter 500 transmits or sends signal 506 into material 504. Signal 506 is a waveform having a selected frequency range. Response 508 is detected by sensor 502. Response 508 is generated in response to the transmission of signal 506 into material 504. Although, in this example, sensor 502 is shown as receiving response 508 on an opposite side of material 504 from transmitter 500, sensor 502 may be located on the same side of material 504 as transmitter 500. With this configuration, response 508 is detected from reflections or scattering of signal 506 being transmitted into material 504.

Response 508 is used, in these different illustrative examples, in a comparison with a simulated response to determine whether changes have occurred in material 504. These changes may be anomalies that occur through various stresses and other environmental conditions to which material 504 is subjected to over time.

Figure 6:
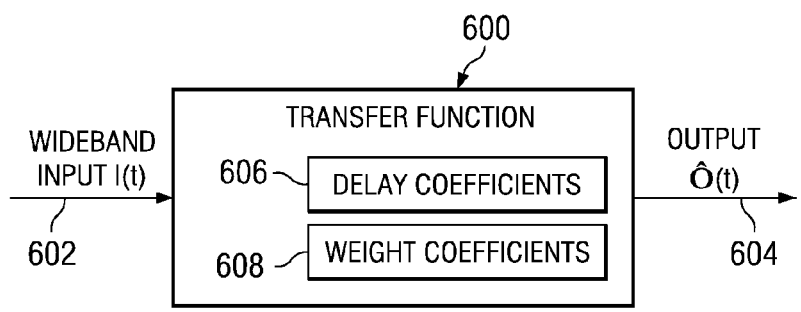
FIG. 6 is a diagram of a functional model in accordance with an advantageous embodiment.

Turning now to FIG. 6, a diagram of a functional model is depicted in accordance with an advantageous embodiment. In this example, transfer function 600 is an example of a component that may be used for functional models 416 in FIG. 4. Transfer function 600 generates a simulated output in response to an input. In particular, in this example, the input into transfer function 600 is wideband input I(t) 602. Output Ô(t) 604 is a simulated output of the response that would actually be received by a sensor to a particular material as being modeled by transfer function 600. In this example, this output is an approximation and may not be an exact output.

Transfer function 600 contains delay coefficients 606 and weight coefficients 608. These different coefficients or transfer function 600 are determined based on output Ô(t) 604 when wideband input I(t) 602 is input into transfer function 600. In these examples, wideband input I(t) 602 takes the form of a set of parameters. This set of parameters may be one or more parameters that are input into transfer function 600 to generate output Ô(t) 604. In these particular examples, delay coefficients 606 and weight coefficients 608 are identified through empirical testing. The actual response, response 508, detected by sensor 502, in response to signal 506, from transmitter 500 in FIG. 5, is used to create transfer function 600, in these examples.

In these examples, the input is a wideband input that has a frequency range that encompasses all of the different frequency ranges that may be used by the different transmitters for sending signals into one or more structures being monitored by a health monitoring system. In these depicted examples, the frequency range of wideband input I(t) 602 encompasses other frequencies if all of those other frequencies are completely within the frequency range of wideband input I(t) 602. Wideband input I(t) 602 is known and input into transfer function 600.

Delay coefficients 606 and weight coefficients 608 are altered until output Ô(t) 604 matches the output of the actual data for the wideband frequency range. Transfer function 600 may be created as follows:

Given I(t): input waveform
O(t): sensor output data $$\hat{O}(t) = \sum_{i=1}^{N} W_i I_i(t) = \sum_{i=1}^{N} W_i I(t - T_i)$$

where Ô(t): approximation of O(t)
$T_i$: Delay coefficient
$W_i$: Weight coefficient
$T_i$, $W_i$ will be searched by cross correlation and reducing the residual error As a result, any transmissions by those two transmitters being received may be detected by the sensor and may be modeled using transfer function 600.

Figure 7:
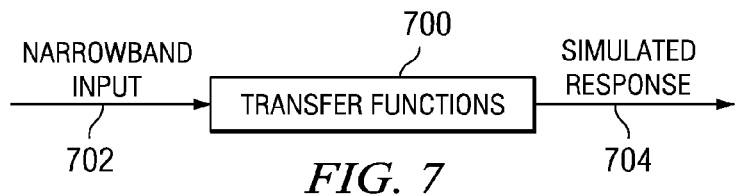
FIG. 7 is a diagram illustrating the use of a transfer function in accordance with an advantageous embodiment.

Turning now to FIG. 7, a diagram illustrating the use of a transfer function is depicted in accordance with an advantageous embodiment. In this illustrative example, transfer function 700 is a transfer function that has a frequency range that encompasses the frequency range of narrowband input 702. As a result, simulated response 704 may be generated to simulate the response that the sensor would perceive from the transmitter. In these examples, transfer function 700 is created for a particular transmitter and sensor.

Consequently, if the same sensor receives or detects signals from a different transmitter, then another transmitter function is required. Of course, the wideband input into the transfer function may be from two transmitters and perceived by a single sensor.

Figure 8:
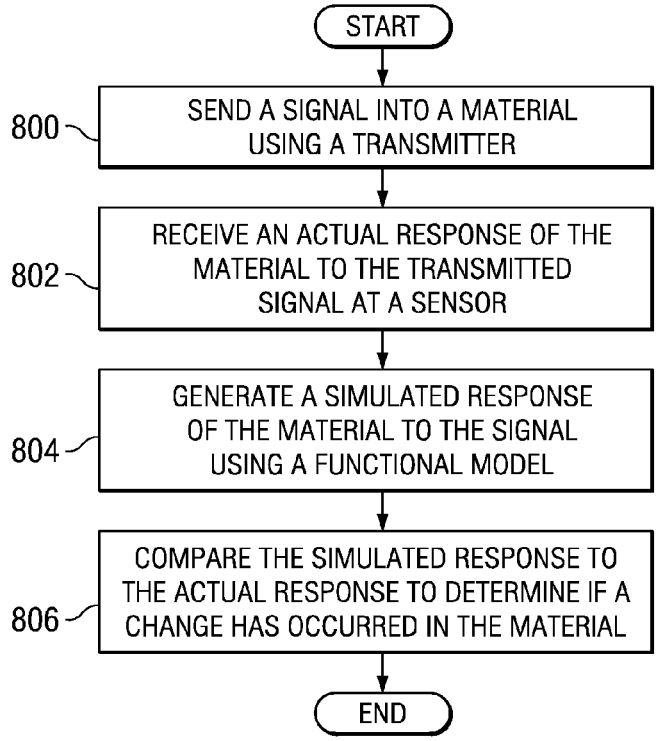
FIG. 8 is a flowchart of a process for testing materials in accordance with an advantageous embodiment.

Turning now to FIG. 8, a flowchart of a process for testing materials is depicted in accordance with an advantageous embodiment. The process illustrated in FIG. 8 may be implemented in a structural health monitoring system, such as structural health monitoring system 408 in FIG. 4.

The process begins by sending a signal into a material using a transmitter (operation 800). The signal has a frequency range that falls within a selected frequency range to form a transmitted signal, in these examples. Next, an actual response of the material to the transmitted signal is received at a sensor (operation 802).

The process generates a simulated response of the material to the signal using a functional model (operation 804). The simulated response is compared to the actual response to determine if a change has occurred in the material (operation 806) with the process terminating thereafter.

Figure 9:
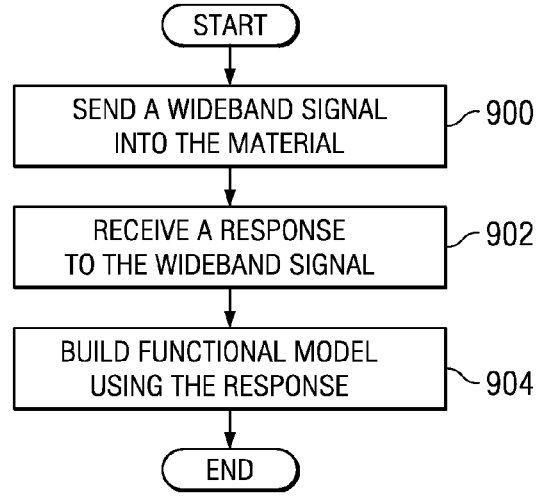
FIG. 9 is a flowchart of a process for building a functional model in accordance with an advantageous embodiment.

Turning now to FIG. 9, a flowchart of a process for building a functional model is depicted in accordance with an advantageous embodiment. In these examples, the process may be implemented in a data processing system, such as data processing system 300 in FIG. 3. The process may be executed before the structural health monitoring system is created or may be processed in the structural health monitoring system that is initially run to create the functional models. The functional models, in these examples, take the form of transfer functions. The functional model can significantly reduce the amount of data storage required by a structural health monitoring system since the transfer function used can reproduce any signal responses within the frequency band used for creating the transfer function.

The process begins by sending a wideband signal into the material (operation 900). This wideband signal has a selected frequency range that encompasses all frequency ranges that may be used in monitoring the material. Next, a response is received to the wideband signal (operation 902).

The functional model is then built using the response (operation 904) with the process terminating thereafter. This functional model is one that is capable of modeling responses to the material at different frequency ranges falling in the selected frequency range for the wideband signals sent into the material in operation 900.

Figure 10:
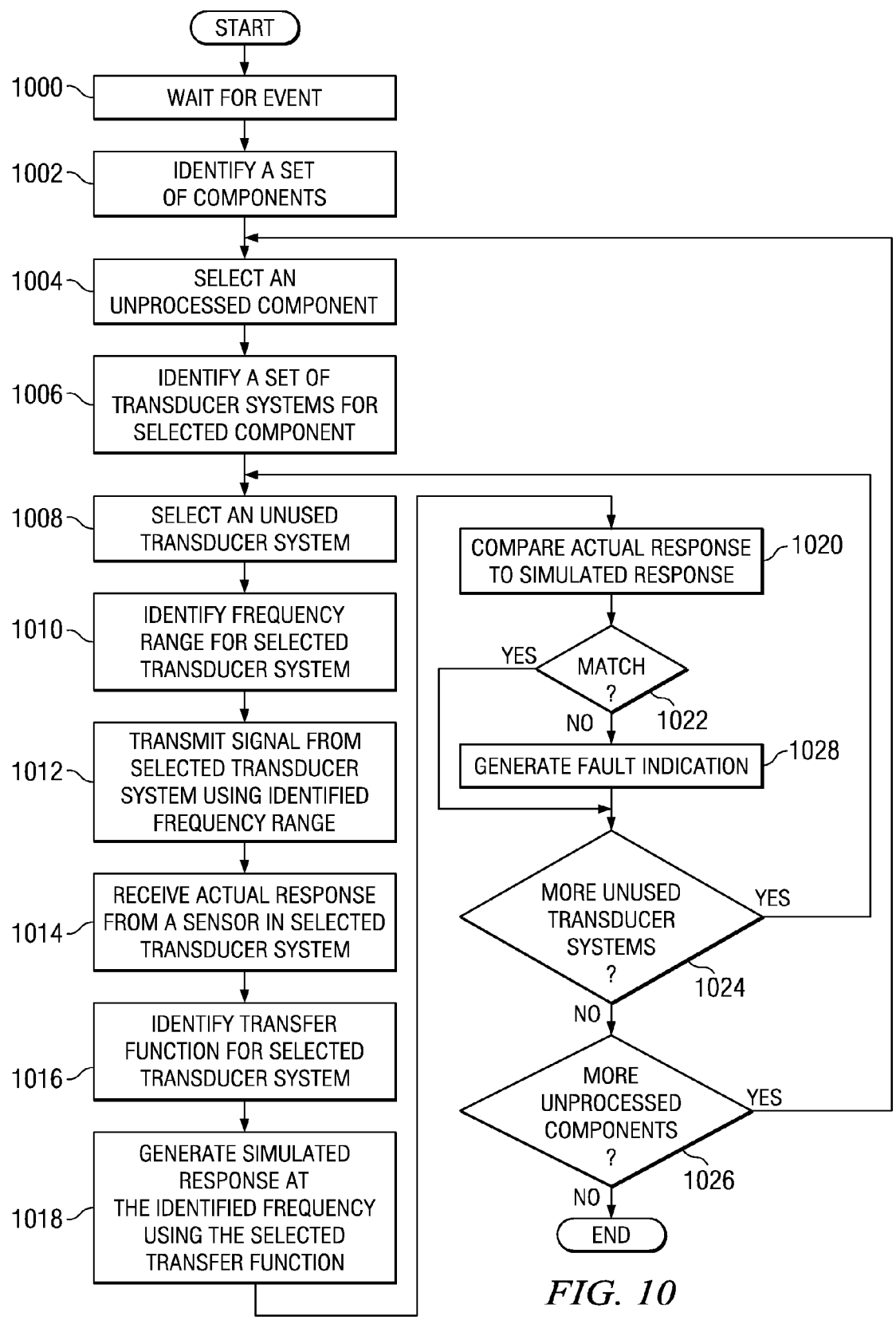
FIG. 10 is a flowchart of a process for monitoring a structure in accordance with an advantageous embodiment.

Turning now to FIG. 10, a flowchart of a process for monitoring a structure is depicted in accordance with an advantageous embodiment. The process illustrated in FIG. 10 may be implemented in a structural health monitoring system, such as structural health monitoring system 408 in FIG. 4.

The process begins by waiting for an event (operation 1000). In these examples, the event may be a periodic event that causes selected components within the structure to be monitored or tested. Alternatively, the event may be a non-periodic event, such as a user input requesting a test of components in the structure. The event also may be, for example, an environmental event, such as an electromagnetic event being applied to the structure. A lightning strike or a power surge is an example.

Thereafter, a set of components is identified (operation 1002). This set of components may be one or more components in the structure. The identification of the set of components may depend on the particular event or may be a preset of components that are tested every time the event occurs. The process then selects an unprocessed component (operation 1004). A set of transducer systems are identified for the selected component (operation 1006).

This set of transducer systems may be one or more transducer systems that are used to test the component. The transducer system may be, for example, a transmit transducer and a receiver transducer. Alternatively, the transducer system may be a single transducer that appoints both functions. Of course, the transducer system may take other configurations. For example, two transmitters may be selected to transmit signals that are detected by a single sensor.

The process then selects an unused transducer system (operation 1008). The process identifies a frequency range for the selected transducer system (operation 1010). The process causes a signal to be transmitted from the selected transducer system using the identified frequency range (operation 1012).

Next, the process receives an actual response from a sensor in the selected transducer system (operation 1014). A transfer function is identified for the selected transducer system (operation 1016). The process then generates a simulated response at the identified frequency using the selected transfer function (operation 1018). The process compares the actual response to the simulated response (operation 1020).

A determination is made as to whether a match is present for this comparison (operation 1022). As described before, a match may occur if the actual response is identical to the simulated response. A match also may be determined to be present if the difference between the actual response and the simulated response are within some range or selected amount of error.

If a match is present, a determination is made as to whether additional unused transducer systems are present (operation 1024). If one or more unused transducer systems have been used for testing the component, the process then returns to operation 1008.

If additional unused transducer systems are not present, the process determines whether unprocessed components are still present in the structure (operation 1026). If additional unprocessed components are present, the process returns to operation 1004 to select another unprocessed component for processing. Otherwise, the process terminates.

With reference again to operation 1022, if a match is not present, a fault indication is generated (operation 1028). The process then proceeds to operation 1024 as described above. In generating a fault indication, the fault indication may be merely an indication that a fault is present. Alternatively, the fault indication may identify other information, such as the component in which the fault indication is detected. Other information, such as the transducer system in which the match was absent, may be included. The actual response received or detected by the sensor in the transducer system also may be included in the fault indication for further processing.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

Thus, the different advantageous embodiments provide a method, apparatus, and computer usable program code for monitoring materials and structures. In the different advantageous embodiments, a signal may be sent into material using a transmitter in which the signal has a frequency range that falls within a selected frequency range to form a transmitted signal. An actual response to the transmitted signal is received at a sensor. A simulated response of the material to the signal using a functional model capable of modeling responses of the material to different frequency ranges falling within the selected frequency range is generated. The simulated response is compared to the actual response to determine if a change has occurred in the material. In this manner, the amount of space needed to store models is reduced through the use of a functional model in which simulated responses are generated.

Although the depicted examples are directed towards sending a signal into a material and comparing a received response to a simulated response, the received response could be from a second transmission or re-transmission of the signal, in these examples. For example, a signal may be transmitted from a transmitter to a sensor. The sensor receiving the response to this signal may function as a transmitter and re-transmit the response back into the material. The transmitter now functions as a sensor and receives a response from the transmitted signal. This received response is an actual response that may be compared to the signal that was originally sent into the material.

In the different illustrative embodiments, this actual response may be the signal generated from a response that was re-transmitted by the receiver or sensor back to the transmitter. The simulated signal may be a simulation of the transmit response, which is compared to the actual response to determine whether changes or anomalies have occurred in the material. This type of re-transmission of the signal is also referred to as a time reversal response, or a time reversal analysis.

In some advantageous embodiments, a transfer function may be created for this type of analysis to simulate the response that is re-transmitted to the transmitter for comparison with a simulated response that should have been received by the transmitter. The different advantageous embodiments may be applied to simulating responses that are expected for a particular material in a particular state, and compare those responses to actual responses to identify whether changes in the material have occurred.

The description of the different advantageous embodiments has been presented for purposes of illustration and description, and is not intended to be exhaustive or limited to the invention in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the invention, the practical application, and to enable others of ordinary skill in the art to understand the invention for various embodiments with various modifications as are suited to the particular use contemplated.

What is claimed is:

1. A method for monitoring structures in a vehicle, the method comprising:
    sending a signal having a frequency range into a structure in the vehicle from a fixed transmitter associated with the structure, wherein the signal has a selected frequency range that encompasses all frequency ranges used to monitor the structure in the vehicle;
    receiving a response to the signal at a fixed sensor associated with the structure;
    creating a transfer function using the response to select a set of delay coefficients and a set of weight coefficient for the transfer function, wherein the transfer function simulates responses to input signals having frequency ranges encompassed by the selected frequency range;
    inputting parameters into the transfer function to simulate sending the signal having the frequency range into the structure by the fixed transmitter;
    responsive to inputting the parameters, receiving a simulated response that simulates the response received by the fixed sensor;
    determining, by a processor, whether the response matches the simulated response; and
    generating a warning indictor if a match between the response and the simulated response is absent.

2. The method of claim 1 further comprising:
    wherein the signal is a wideband signal;
    receiving a test response to the wideband signal at the fixed sensor; and
    creating the transfer function using the test response, wherein the transfer function simulates responses to input signals having frequency ranges encompassed by the selected frequency range.

3. The method of claim 2, wherein the creating the transfer function using the test response further comprises:
    creating the transfer function using the test response in which the transfer function uses the following:

$$\hat{O}(t) = \sum_{i=1}^{N} W_i I_i(t) = \sum_{i=1}^{N} W_i I(t - T_i)$$

where (t) represents the simulated response, I(t) is a wideband input signal, $T_i$ is the delay coefficient, and $W_i$ is the weight coefficient and wherein the transfer function simulates responses to input signals having frequency ranges encompassed by the selected frequency range.

4. The method of claim 1 further comprising:
    sending a second signal having a second frequency range into another portion of the structure in the vehicle from a second fixed transmitter associated with the second structure;
    receiving a second response to the second signal at a second fixed sensor associated with the another portion of the structure;
    inputting second parameters into a second transfer function to simulate sending the signal having the frequency range into the another portion of the structure by the second fixed transmitter;
    responsive to inputting the second parameters, receiving a second simulated response that simulates the second response received by the second fixed sensor;
    determining whether the second response matches the second simulated response; and
    generating the warning indictor if a second match between the second response and the second simulated response is absent.

5. The method of claim 1 further comprising:
    sending a second signal having the a second frequency range into the structure in the vehicle from a second fixed transmitter associated with the structure;

receiving a second response to the second signal at the fixed sensor associated with the structure;

inputting second parameters into a second transfer function to simulate sending the second signal having the second frequency range into the structure by the second fixed transmitter;

responsive to inputting the second parameters, receiving a second simulated response that simulates the second response received by the fixed sensor;

determining whether the second response matches the second simulated response; and generating the warning indictor if a second match between the second response and the second simulated response is absent.

6. The method of claim 1, wherein sending the signal comprises:

sending a wideband signal into the structure in the vehicle, wherein the wideband signal has a selected frequency range that encompasses all frequency ranges used to monitor the structure in the vehicle, wherein the vehicle is one of an aircraft, a car, a tank, a ship, a submarine, or a spacecraft.

* * * * *